(12) United States Patent
Schmitz (10) Patent No.: US 11,872,004 B2
(45) Date of Patent: Jan. 16, 2024

(54) UNIVERSAL JOINT FOR SURGICAL ROBOTICS

(71) Applicant: Gregory P. Schmitz, Los Gatos, CA (US)

(72) Inventor: Gregory P. Schmitz, Los Gatos, CA (US)

(73) Assignee: Syncrobotix, Inc., Los Gatos, CA (US)

( * ) Notice: Subject to any disclaimer, the term of this patent is extended or adjusted under 35 U.S.C. 154(b) by 0 days.

(21) Appl. No.: 18/110,925

(22) Filed: Feb. 17, 2023

(65) Prior Publication Data

US 2023/0190393 A1 Jun. 22, 2023

Related U.S. Application Data

(62) Division of application No. 17/318,617, filed on May 12, 2021, now abandoned, which is a division of application No. 16/270,714, filed on Feb. 8, 2019, now Pat. No. 11,033,342.

(60) Provisional application No. 62/632,031, filed on Feb. 19, 2018.

(51) Int. Cl.
*A61B 34/30* (2016.01)
*A61B 34/00* (2016.01)
*H02K 15/00* (2006.01)

(52) U.S. Cl.
CPC ............. *A61B 34/30* (2016.02); *H02K 15/00* (2013.01); *A61B 2034/306* (2016.02); *A61B 2034/715* (2016.02)

(58) Field of Classification Search
CPC .............. A61B 34/30; A61B 2034/306; A61B 2034/715
See application file for complete search history.

(56) References Cited

U.S. PATENT DOCUMENTS

| 11,033,342 B2 | 6/2021 | Schmitz |
| 2008/0275300 A1* | 11/2008 | Rothe ................ A61B 1/00006 600/129 |
| 2012/0143173 A1 | 6/2012 | Steege |
| 2017/0095922 A1 | 4/2017 | Licht |
| 2019/0254760 A1 | 8/2019 | Schmitz |
| 2021/0322113 A1 | 10/2021 | Schmitz |

OTHER PUBLICATIONS

U.S. Appl. No. 16/270,714 U.S. Pat. No. 11,033,342, filed Feb. 8, 2019, Universal Joint for Surgical Robotics.
U.S. Appl. No. 17/318,617, filed May 12, 2021, Universal Joint for Surgical Robotics.
"U.S. Appl. No. 16/270,714, Non Final Office Action dated Dec. 21, 2020", 8 pgs.
"U.S. Appl. No. 16/270,714, Notice of Allowance dated Mar. 19, 2021", 8 pgs.

(Continued)

*Primary Examiner* — Paula J Stice
(74) *Attorney, Agent, or Firm* — Stephen E. Zweig (57) ABSTRACT

In an example, there is provided a method for manipulating a robotic surgery tool, the method comprising: applying tension to a first pull wire to cause a first link of a joint device of the tool to pivot in a first plane relative to a yoke attached to the first link; and applying tension to a second pull wire to cause a second link attached to the yoke to pivot in a second plane orthogonal to the first plane.

9 Claims, 8 Drawing Sheets

(56) References Cited

OTHER PUBLICATIONS

"U.S. Appl. No. 16/270,714, Response filed Mar. 2, 2021 to Non Final Office Action dated Dec. 21, 2020", 13 pgs.
"U.S. Appl. No. 16/270,714, Response filed Nov. 9, 2020 to Restriction Requirement dated Oct. 30, 2020", 1 pg.
"U.S. Appl. No. 16/270,714, Restriction Requirement dated Oct. 30, 2020", 7 pgs.
"U.S. Appl. No. 17/318,617, Preliminary Amendment filed May 12, 2021", 5 pgs.
"U.S. Appl. No. 17/318,617, Restriction Requirement dated Jan. 10, 2023", 5 pgs.

* cited by examiner

UNIVERSAL JOINT FOR SURGICAL ROBOTICS

CROSS-REFERENCE TO RELATED APPLICATIONS

This application is a divisional application of U.S. patent application Ser. No. 17/318,617, filed May 12, 2021, now abandoned; application Ser. No. 17/318,617 was a divisional application of U.S. patent application Ser. No. 16/270,714, filed Feb. 8, 2019, now U.S. Pat. No. 11,033,342, issued May 26, 2021; application Ser. No. 16/270,714 claims the benefit of U.S. Provisional Patent Application No. 62/632,031, filed Feb. 19, 2018, entitled, "UNIVERSAL JOINT FOR SURGICAL ROBOTICS;" The entire contents of all of these disclosures are incorporated herein by reference.

TECHNICAL FIELD

This application is related to medical devices, systems and methods. More specifically, the application is related to a universal wrist or joint for use with a surgical robotic system.

BACKGROUND

Robotic surgery has become steadily more prevalent in recent years. In some cases, robotic surgery may provide greater levels of precision or allow for smaller incisions than conventional surgery. Robotic surgery systems are generally large, complex machines, costing in the millions of dollars, such as the da Vinci® Surgical System, from Intuitive Surgical, Inc. (intuitivesurgical.com). These robotic surgery systems typically include multiple arms or "end effectors," which the physician controlling the system can manipulate, using controllers, to perform a surgical procedure. To be effective, the end effectors must be very controllable, precise and accurate, and they must often be quite small (in diameter) to fit through small incisions or bodily openings.

Tool developers for surgical robotic systems are ever striving to reduce the cross-sectional area of their instruments, while maintaining the same freedom of movement, precision and control as larger instruments. As the tools get smaller, however, the precision of the tools must increase to achieve higher levels of control and more freedom of movement.

BRIEF SUMMARY

A joint device for a robotic surgery tool includes a yoke and two links movably coupled with the yoke. The yoke may include a circumferential base, forming a central opening and four cylindrical pivot bosses extending laterally from the base at ninety-degree intervals. A first link is movably coupled with a first set of two of the four cylindrical pivot bosses and extends from the yoke in a first direction, such that the first link pivots in a first plane relative to the yoke. A second link is movably coupled with a second set of two of the four cylindrical pivot bosses and extends from the yoke in a second direction, such that the second link pivots in a second plane orthogonal to the first plane. Thus, the joint device provides for movement in two opposed planes from one yoke. The pivot axes of the links intersect each other through the center of the yoke. In other words, the yoke's pivot points are always perpendicular to the neutral axis. This is completely different than currently available robotic surgery joints or wrists, which require at least three links and the axes of pivots of the links do not intersect each other.

The joint device described herein may have a number of advantages over currently available systems. For example, the joint allows for manufacture of a robotic surgery tool having an outer diameter of 10 mm or at a lower cost than currently available devices. Control cables (or "pull wires") pass through thin, low friction holes in the yoke of the joint. The pull wires are also located near the periphery of the yoke, thus providing high levels of torque and allowing for a large central opening in the yoke and the device generally, to allow tools to pass through. The neutral axis is tightly maintained to the driven radius of curvature, since the yoke has intersecting pivots for direction of articulation. Additionally, the joint provides a constant velocity system with improved precision and control versus currently available systems.

In one aspect of the present application, a joint device for a robotic surgery tool includes a yoke, a first link and a second link. The yoke includes a circumferential base, forming a central opening, and four cylindrical pivot bosses extending laterally from the base at ninety-degree intervals. The first link is movably coupled with a first set of two of the four cylindrical pivot bosses and extends from the yoke in a first direction, such that the first link pivots in a first plane relative to the yoke. The second link is movably coupled with a second set of two of the four cylindrical pivot bosses and extends from the yoke in a second direction, such that the second link pivots in a second plane orthogonal to the first plane.

In some embodiments, the first link includes a first ring, a first set of arms extending vertically from the first ring in a first direction, and a second set of arms extending vertically from the first ring in a second, opposite direction. Similarly, the second link may include a second ring, a third set of arms extending vertically from the second ring in a first direction, and a fourth set of arms extending vertically from the second ring in a second, opposite direction. In such embodiments, each arm includes a circular hole sized to fit over one of the four cylindrical pivot bosses of the yoke. In some embodiments, the first set of cylindrical pivot bosses are on opposite sides of the yoke from one another, and the second set of cylindrical pivot bosses are on opposite sides of the yoke from one another. In some embodiments, an outer surface of the base of the yoke forms four straight sides forming a square. The base of the yoke may also include four vertically oriented pull wire holes disposed at ninety-degree intervals from one another. In some embodiments, an outer diameter of the first link and the second link is no more than about 10 millimeters.

In another aspect of the present disclosure, a joint for use in a tool of a robotic surgical system may include a first link, a second link, and a yoke disposed between the first and second links. The first link, second link, and yoke may have the features described above.

In another aspect of the present application, a robotic surgery tool may include a joint and an end effector. The joint may have any of the features described above. The robotic surgery tool may include any number of joints, such as only one joint, two joints, three joints, or any other number. In some embodiments, a significant length of the tool may be made up of joints, attached to one another in a chain. Thus, the robotic surgery tool may include at least one additional yoke coupled to the first link or the second link, at least one additional link coupled to the additional yoke, and so on.

In some embodiments, the base of the yoke includes four vertically oriented pull wire holes disposed at ninety-degree intervals from one another, and the robotic surgery tool further includes four pull wires disposed individually in each of the four pull wire holes. The four pull wires may be attached at one end to the end effector and at an opposite end to a manipulator for applying tension to the four pull wires. According to various embodiments, any suitable end effector may be included on the robotic surgery tool. For example, the end effector may include, but is not limited to, a camera, a light emitter, an injection needle, a needle biopsy device, a brush biopsy device, forceps, a tissue debrider, scissors, a scalpel, a suture needle holder, an electrocautery device, a coagulation device, a radiofrequency device or a probe. In some embodiments, the end effector extends from a distal end of the robotic surgery tool through the central opening of the yoke toward a proximal end of the robotic surgery tool. Optionally, the robotic surgery tool may also include multiple additional joints coupled with the joint and a drive shaft extending through the central opening of the joint and additional central openings of the additional joints.

In another aspect of the present application, a method for manufacturing a joint device for a robotic surgery tool may involve: providing a first link and a second link; manufacturing a yoke; coupling the first link with the yoke by sliding the holes of one of the sets of arms over a first set of two opposed pivot bosses of the four cylindrical pivot bosses; and coupling the second link with the yoke by sliding the holes of one of the sets of arms over a first set of two opposed pivot bosses of the four cylindrical pivot bosses. Again, the first link, second link, and yolk may have any of the features described above. In some embodiments, providing the first link and the second link involves laser cutting the first link and the second link out of one or more hypotubes. In some embodiments, providing the yoke comprises machining the yoke. In other embodiments, the yoke may be metal injection molded. In some embodiments, the first link and/or the second link may be manufactured by 3D printing. In various embodiments, the first link, the second link and/or the yoke may be manufactured from materials such as, but not limited to, stainless steel, titanium, Nitinol and/or aluminum.

In yet another aspect of the present application, a method for manipulating a robotic surgery tool may involve applying tension to a first pull wire to cause a first link of a joint device of the tool to pivot in a first plane relative to a yoke attached to the first link and applying tension to a second pull wire to cause a second link attached to the yoke to pivot in a second plane orthogonal to the first plane. As mentioned above, the robotic surgery tool in any given embodiment may include more than one joint. The method also typically, but not necessarily, includes performing a function with an end effector of the robotic surgery tool. The end effector often extends from a distal end of the robotic surgery tool toward a proximal end through a central opening in the yoke. Any end effector may be used, such as but not limited to those listed above.

In some embodiments, the first and second pull wires extend from the end effector to a pull wire manipulator at or near a proximal end of the robotic surgery device, so that applying tension to the first and second pull wires applies force to the end effector, which is transmitted to the joint device. In some embodiments, applying the tension to the first pull wire and/or the second pull wire causes at least a third link to pivot relative to at least one additional yoke. The method of manipulating the device may be part of performing a procedure, such as but not limited to debrider tumor resection, shears tumor resection, delivery of biologics and medications, neural tumor resection, polyp resection or biopsy, breast biopsy, lung biopsy, minimal portal access heart bypass, endoscopic submucosal dissection, transurethral procedures (TURP, bladder tumors) prostatectomy, hysterectomy, stem cell delivery, delivery of arthroscopic tools, knees and hips, or transnasal procedures (frontal sinus tissue removal, functional endoscopic sinus surgery, etc.)

These and other aspects and embodiments are described in greater detail below, in reference to the attached drawing figures.

DETAILED DESCRIPTION

This application describes a universal joint device for a robotic surgery tool. The application also describes various embodiments of robotic surgery tools including one or more of the universal joints. Additionally, the application describes methods for manufacturing the joint device and using a robotic surgery tool that has one or more of the universal joints. In this application, the terms "joint" and "joint device" are used interchangeably, and any other suitable term may be used in place of "joint," such as "wrist." Furthermore, although a number of exemplary embodiments are described below, these are provided as examples only. The universal joint described herein may be used in any suitable medical, surgical or other device and is not limited to use in robotic surgery tools.

Figure 1:
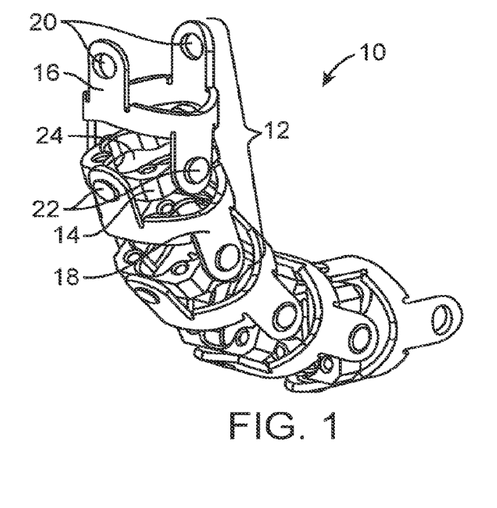
FIG. 1 is a perspective view of a portion of a robotic surgery tool, including multiple link-yoke-link joints, according to one embodiment.
Figure 2:
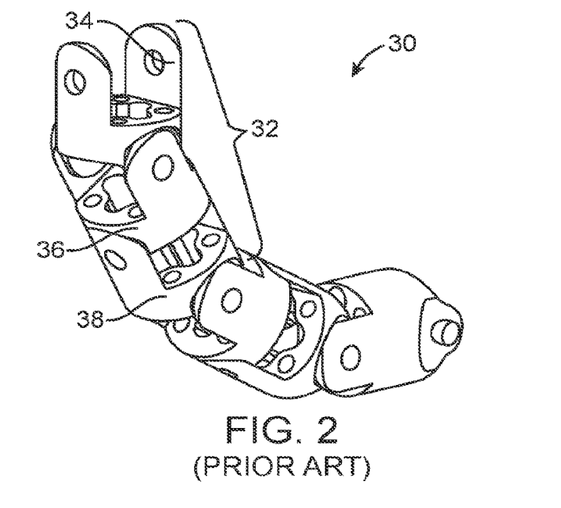
FIG. 2 is a perspective view of a portion of a prior art robotic surgery tool, including multiple prior art three-link joints.
Figure 3:
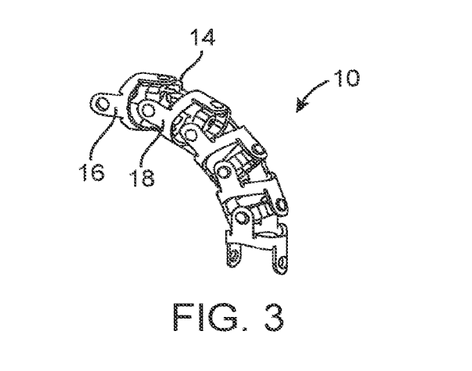
FIGS. 3 and 4 are additional perspective views of the portion of the robotic surgery tools of FIGS. 1 and 2, respectively.
Figure 4:
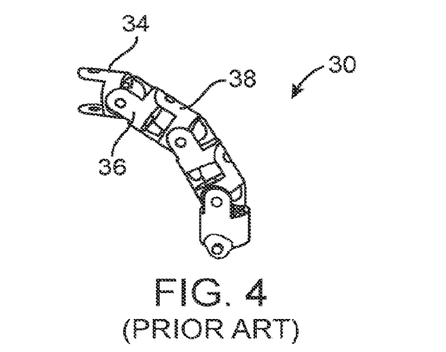
Figure 5:
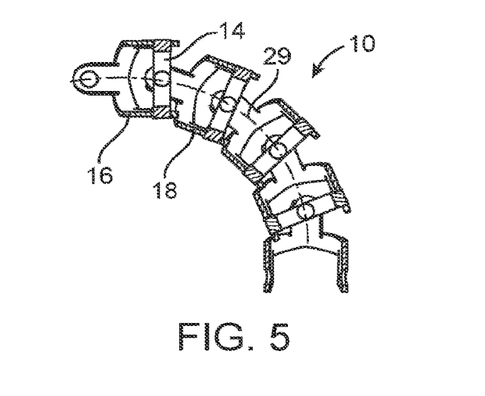
FIGS. 5 and 6 are side views of the portion of the robotic surgery tools of FIGS. 1 and 2, respectively, illustrating the different bending shapes and radii of curvature of the two tools.
Figure 6:
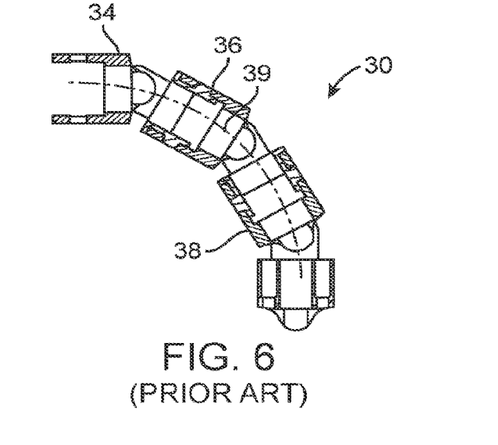

Referring first to FIGS. 1-6, several views of a portion of a robotic surgery device 10 according to one embodiment are shown (FIGS. 1, 3 and 5), alongside corresponding views of a portion of a prior art device 30 (FIGS. 2, 4, 6). The robotic surgery device 10 includes multiple universal joints 12, although in alternative embodiments the device 10 may include any number of joints 12 and as few as one joint 12. Each joint 12, which will be described in further detail below, includes a yoke 14, a first link 16 and a second link 18. The joint 12 may thus be referred to herein as a "link-yoke-link joint." The yoke 14 has a generally square-shaped outer surface (although other shapes are possible), with four cylindrical pivot bosses 22 extending laterally from the four sides of the square. The first link 16 and the second link 18 attach to the yoke 14 via holes 20 that fit over the pivot bosses 22. The holes 20 are sized so that each of the links 16, 18 is able to slide/rotate over the pivot bosses 22 and thus pivot relative to the yoke 14. The first link 16 pivots in a first plane, and the second link 18 pivots in a second plane, orthogonal to the first plane. Thus, the joint 12 is able to bend in two opposed directions or planes at the same linkage location—i.e., at one yoke 14. This movement ability is highly advantageous. The yoke 14 also includes a large central opening 24, which allows elongate tools or portions of tools to pass through the center of the robotic surgery device 10 from one end to an opposite end.

The prior art device 30 (FIGS. 2, 4 and 6) has a completely different linkage system. Here, the joint 32 simply includes three links 34, 36, 38, joined together in succession. There is no equivalent to the yoke 14 of the joint 12 described above, and thus the joint 32 cannot pivot in two directions from one pivot plane. Instead, in this prior art joint 32, a first link 34 pivots in one direction relative to a second link 36, and a third link 38 pivots in an opposed direction relative to the second link.

As shown in the comparison FIGS. 5 and 6, the currently described joint 12 allows the device 10 to have a tighter radius of curvature 29 than a corresponding radius 39 of the prior art device 30. Additionally, the link-yoke-link joints 12 allow the device 10 to tightly follow the radius of curvature 29, with the neutral axis passing through pivot points of each yoke 14. By contrast, the prior device 30 is discontinuous with the neutral axis and the radius of curvature 39. The link-yoke-link joint 12 thus provides for smoother curving/bending ability and increased strength through the curve.

In larger currently available/prior art three-link devices 30, such as devices used for performing colonoscopy, the parts are made from sheet metal rings, pressed together with pins at the pivot points. For smaller-diameter devices, the parts are machined or 3-D printed, because pinning is not feasible at a smaller scale. These machining and printing methods for fabricating linkages at the smaller scale (e.g., under 10 mm diameter) have significant technical challenges: cost goes up beyond an affordable level and precision and control start to diminish. The link-yoke-link joint 12 and device 10 described in this application may solve some of these technical challenges.

Figure 7:
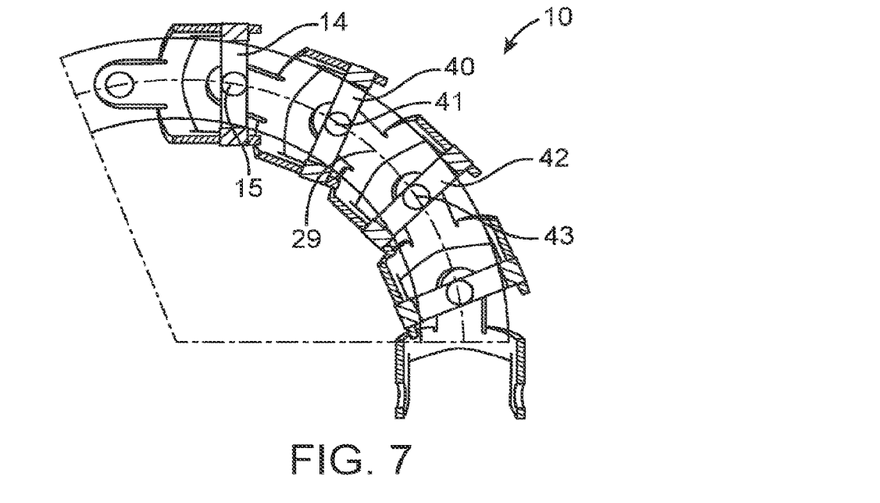
FIGS. 7 and 8 are side, cross-sectional views of the portion of the robotic surgery tool of FIG. 5, illustrating how the centers of the yokes of the tool pass through a radius of curvature.
Figure 8:
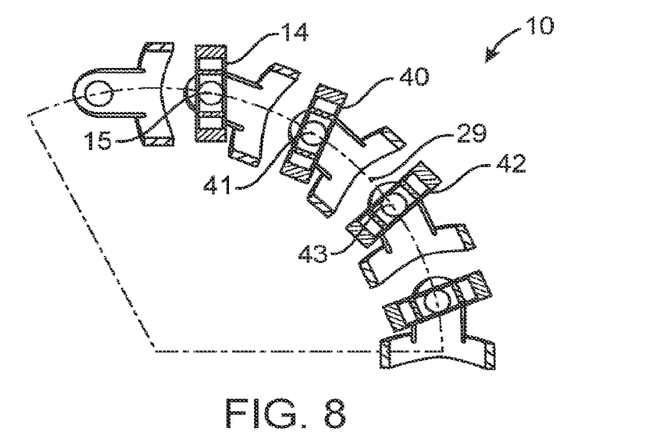

FIGS. 7 and 8 are two different side, cross-sectional views of the same device 10 as in FIGS. 1, 3 and 5, further illustrating the ability of the device 10 to bend smoothly along a radius of curvature. In these figures, two additional yokes 40, 42 are labeled, as are pivot points 15, 41, 43 of the three labeled yokes 14, 40, 42. As illustrated in FIGS. 7 and 8, the radius of curvature 29 of the device 10 passes through all the pivot points 15, 41, 43 of the yokes 14, 40, 42.

Figure 9:
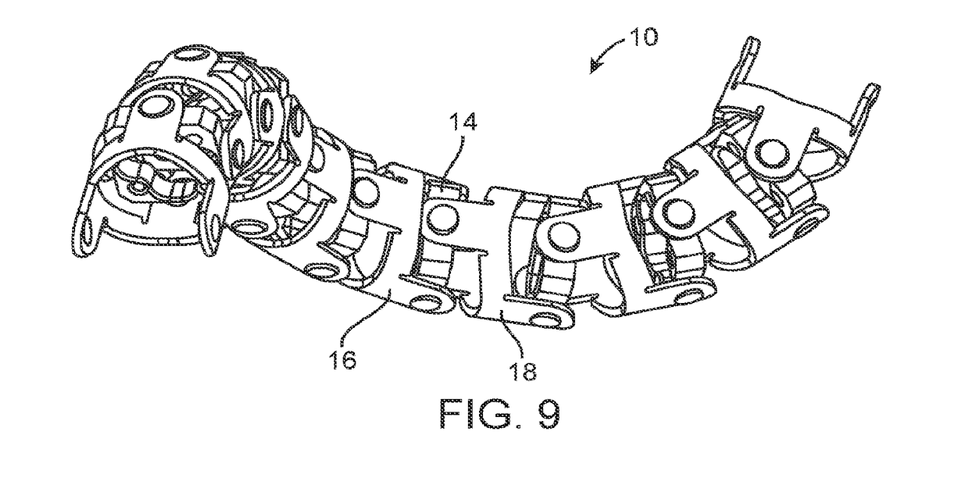
FIG. 9 is a perspective view of a longer portion of the robotic surgery tool of FIG. 1.

FIG. 9 simply illustrates a longer portion of the robotic surgery device 10. In various embodiments, the device 10 may have any length and include any number of joints 12, from as few as one joint to as many as desired. The device 10 may similarly have any suitable outer and inner diameters, according to various embodiments. In some embodiments, for example, the device 10 may have an outer diameter of 10 mm or less. In other words, the outer diameters of the links 16, 18 may be 10 mm or less. The smaller the diameter, the harder the device 10 is to manufacture. However, the link-yoke-link joint 12 makes smaller diameter devices 10 possible and more effective. Manufacturing techniques for the devices 10, including smaller diameter embodiments, are described further below.

Figure 10:
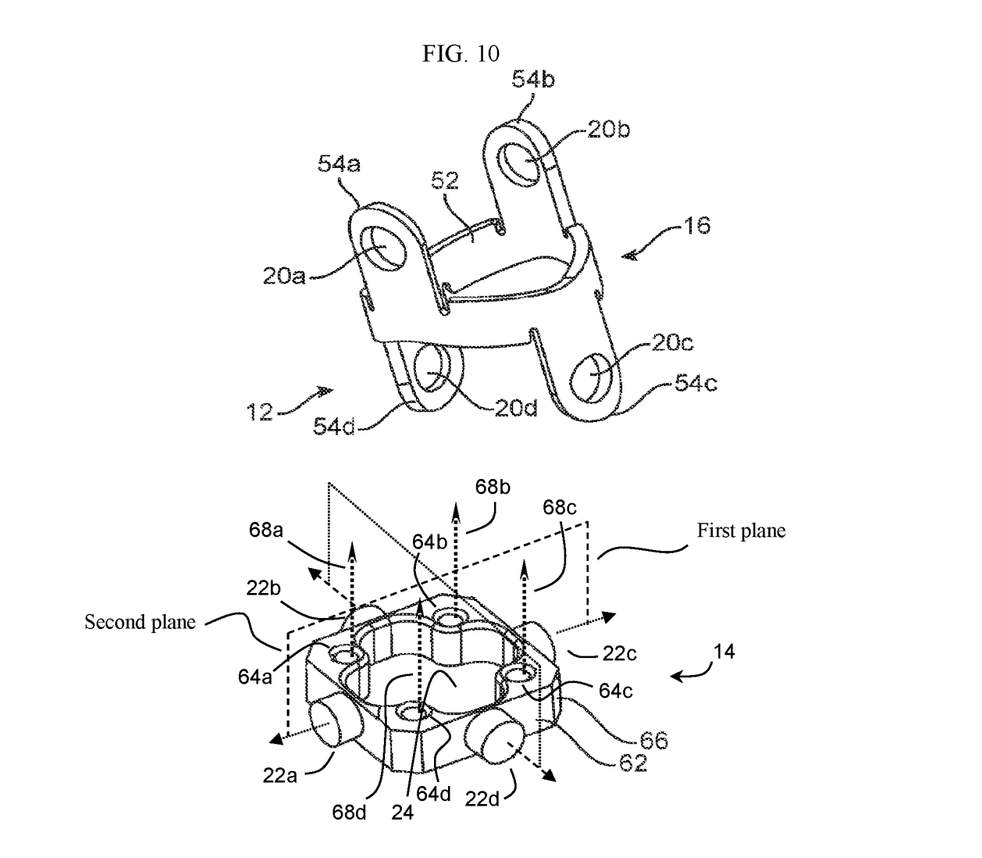
FIG. 10 is an exploded/unassembled view of a link and a yoke of a joint device, according to one embodiment.

Referring now to FIG. 10, the first link 16 and the yoke 14 of the joint 12 are illustrated in greater detail. The first link 16 (and the second link 18, which is not pictured here for ease of illustration) includes a ring 52 and four arms 54a, 54b, 54c, 54d extending from the ring 52, two arms 54a, 54b extending in one direction, and two arms 54c, 54d extending in the opposite direction. Each of the arms 54a, 54b, 54c, 54d has a circular hole 20a, 20b, 20c, 20d. The yoke 14 includes a circumferential base 62, with a generally square outer surface shape and defining the central opening 24 on the inside. In this embodiment, each outer corner 66 of the base 62 is squared off at a 45-degree angle. This is an optional shape, and in alternative embodiments the corners 66 may be rounded, the outer surface may be a complete square, or any other shape may be used. Each outer side has a pivot boss 22a, 22b, 22c, 22d. Additionally, four pull wire holes 64a, 64b, 64c, 64d extend vertically through four corners of the base 62 from top to bottom. These pull wire holes 64a, 64b, 64c, 64d are designed to allow pull wires of the robotic surgery device 10 to pass and slide through them, for controlling bending of the device 10.

To assemble the joint 12, one set of arms 54c, 54d of the first link 16 is passed over opposing sides of the yoke 14, so that two opposed pivot bosses 22b, 22d pass through two corresponding holes 20d, 20c. The second link 18 (not shown in FIG. 10) would similarly be attached to the two remaining free pivot bosses 22a, 22c, thus completing the link-yoke-link structure. The yoke 14 and the two links 16, 18 may be made out of any suitable material or combination of materials, such as but not limited to metals, such as stainless steel, titanium, Nitinol or aluminum, or any suitable polymer. In various embodiments, the links 16, 18 may be manufactured by laser cutting the parts out of a hypotube, machining the parts from a solid, metal injection molding ("MIM") the parts or 3D printing the parts. In one embodiment, the links 16, 18 are made by laser cutting, which may be a preferred method for efficiency and/or cost. The yoke 14 may be manufactured by machining, MIM, or 3D printing. Machining or MIMing may be preferred for cost reasons. Using these manufacturing techniques, joints 12 and device 10 may be made efficiently and with high precision even with small outer diameters, such 10 mm or less or even 6 mm or less.

Figure 11:
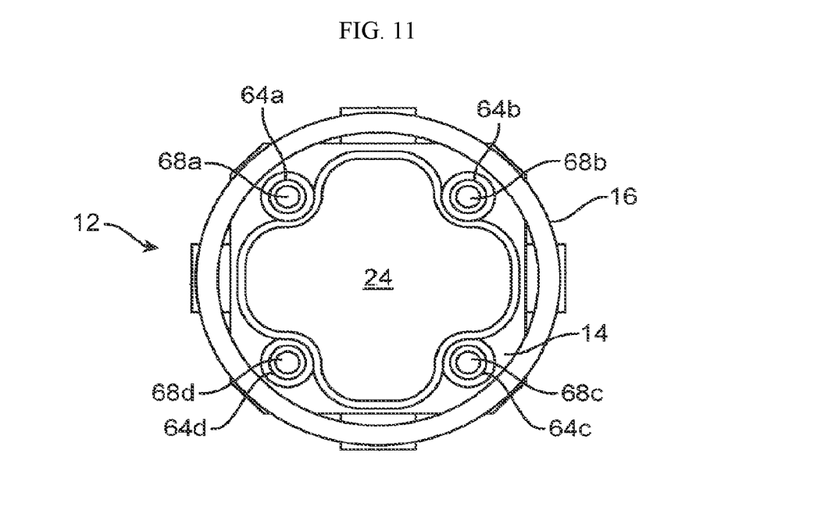
FIG. 11 is a top/assembled view of the link and yoke of the joint device of FIG. 10.
Figures 12A, 12B:
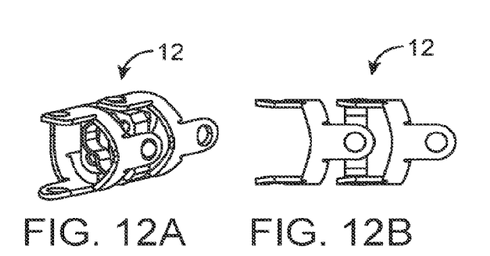
FIGS. 12A-12J are multiple views from different angles of a single link-yoke-link joint, according to one embodiment.
Figure 12C:
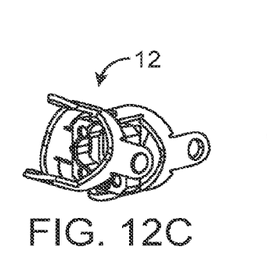
Figure 12D:
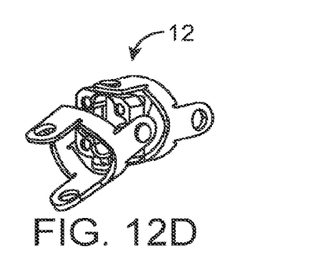
Figure 12E:
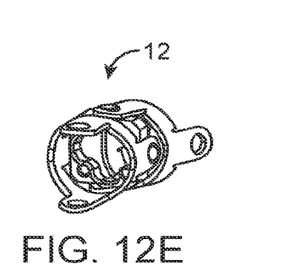
Figure 12F:
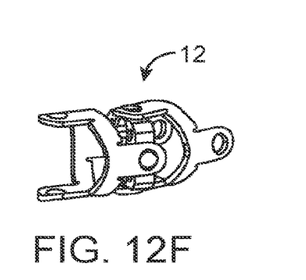
Figure 12G:
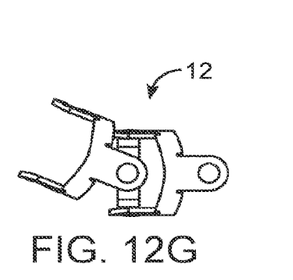
Figure 12H:
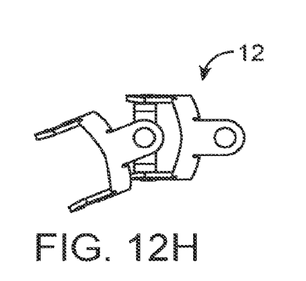
Figure 12I:
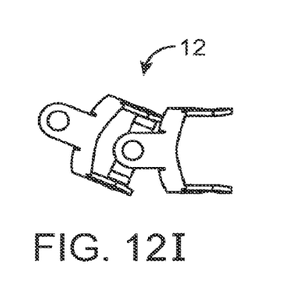
Figure 12J:
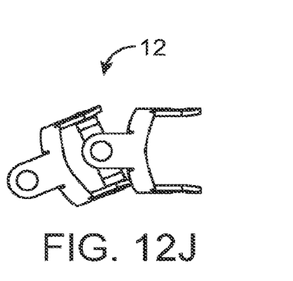

Referring now to FIG. 11, a top view of an assembled portion of the joint 12 is provided. All of the labeled parts are the same as in FIG. 10, with the addition in this figure of showing four pull wires 68a, 68b, 68c, 68d in the four pull wire holes 64a, 64b, 64c, 64d. Pull wires 68a, 68b, 68c, 68d are commonly used in bendable robotic surgery tools for manipulating (bending, twisting, etc.) the tool. They typically run from a proximal end of the tool, where there is a drive mechanism, to a distal end of the tool, where there is an end effector. Applying tension to one or more of the pull wires 68a, 68b, 68c, 68d causes the device to curve or bend in a desired direction. Locating the pull wire holes 64a, 64b, 64c, 64d near the periphery of the joint 12 allows for greater force transfer from the proximal to the distal end compared to at least some prior art devices.

FIGS. 12A-12J show a number of different view of the link-yoke-link joint 12 described previously. These figures illustrate the simple motion of one link relative to the yoke.

Figure 13:
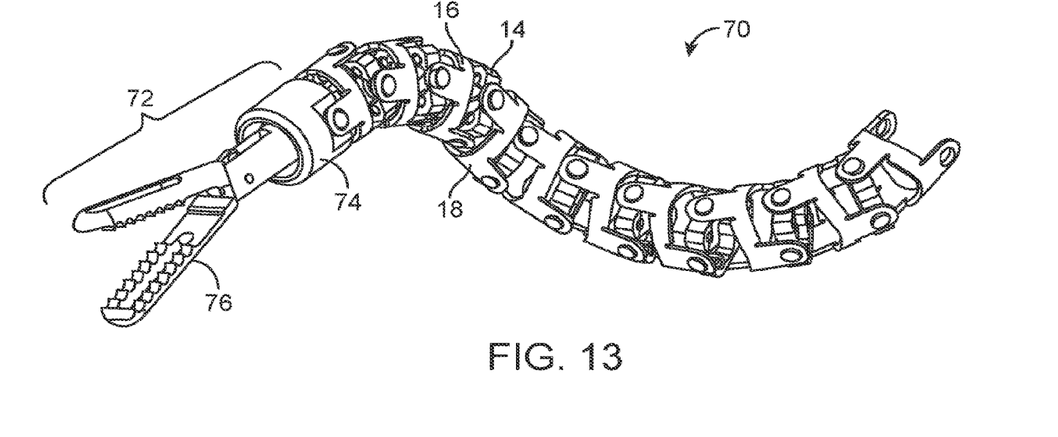
FIG. 13 is a perspective view of a portion of a robotic surgery tool, including multiple joints and a grasper end effector, according to one embodiment.

FIG. 13 is a perspective view of a more complete distal portion of a robotic surgery tool 70, according to one embodiment. The tool includes multiple joints 12, each including a yoke 14, a first link 16 and a second link 18. At the distal end, the device 70 includes an end effector 72, which in this case includes a distal end-piece 74 and a grasper 76. The pull wires of the device 70, which are not visible in FIG. 13, may attach to the distal end-piece and thus apply tension to that component, with the pull forces being transferred proximally to the joints 12.

Figure 14:
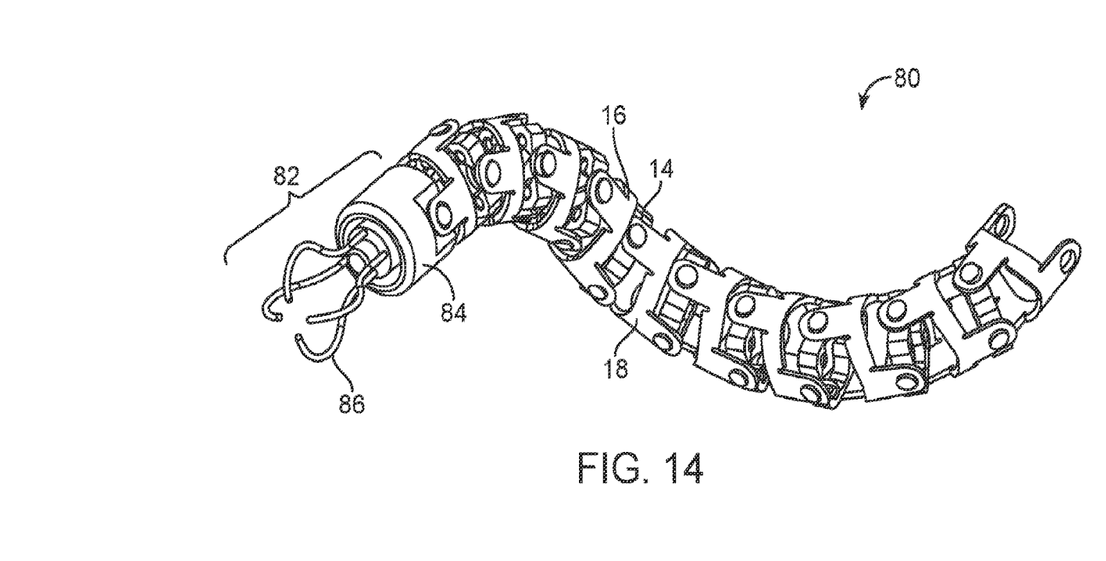
FIG. 14 is a perspective view of a portion of a robotic surgery tool, including multiple joints and a four-wire grasping cage end effector, according to one embodiment.

FIG. 14 is a perspective view of a distal portion of a different embodiment of a robotic surgery tool 80, with the same configuration of joints 12 but with a different end effector 82. In this embodiment, the end effector 82 includes a distal end-piece 84 and a four-wire grasping cage 86.

Figure 15:
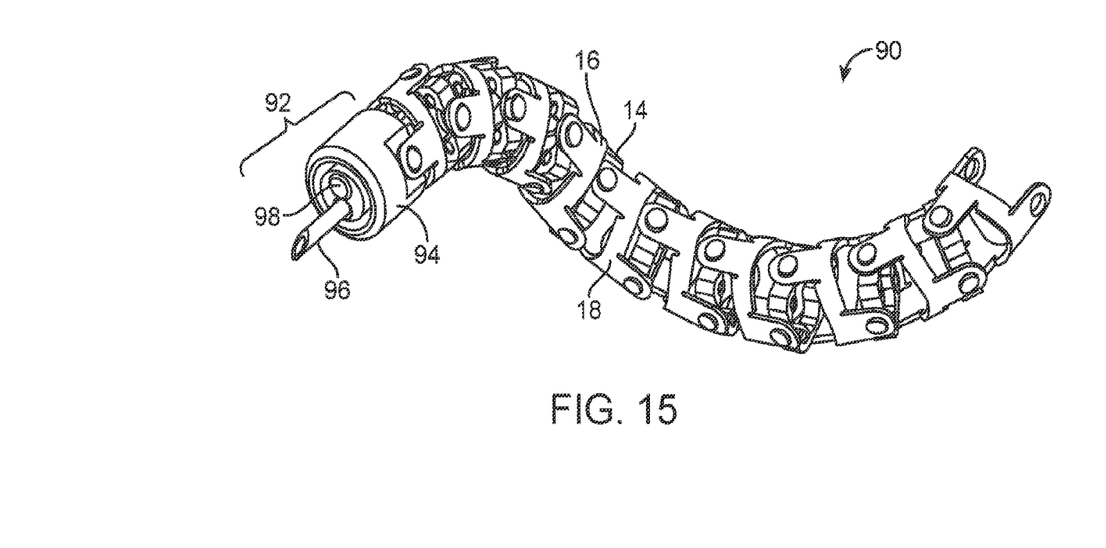
FIG. 15 is a perspective view of a portion of a robotic surgery tool, including multiple joints and a four-wire grasping cage end effector, according to one embodiment.

FIG. 15 is a perspective view of a distal portion of a different embodiment of a robotic surgery tool 90, with the same configuration of joints 12 but with a different end effector 92. In this embodiment, the end effector 92 includes a distal end-piece 94, a biopsy needle 96 and a camera 98.

Figure 16:
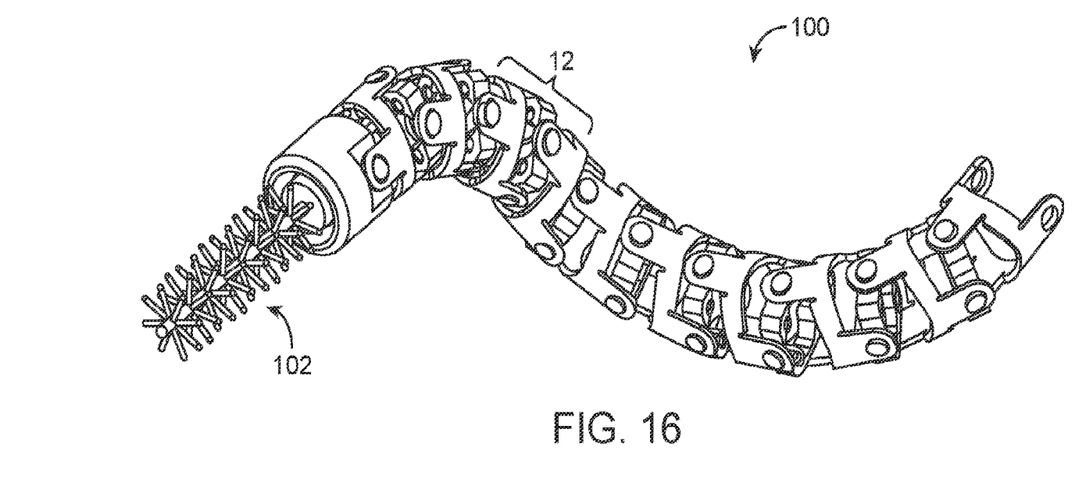
FIG. 16 is a perspective view of a portion of yet another embodiment of a robotic surgery tool, with a biopsy brush end effector.
Figure 17:
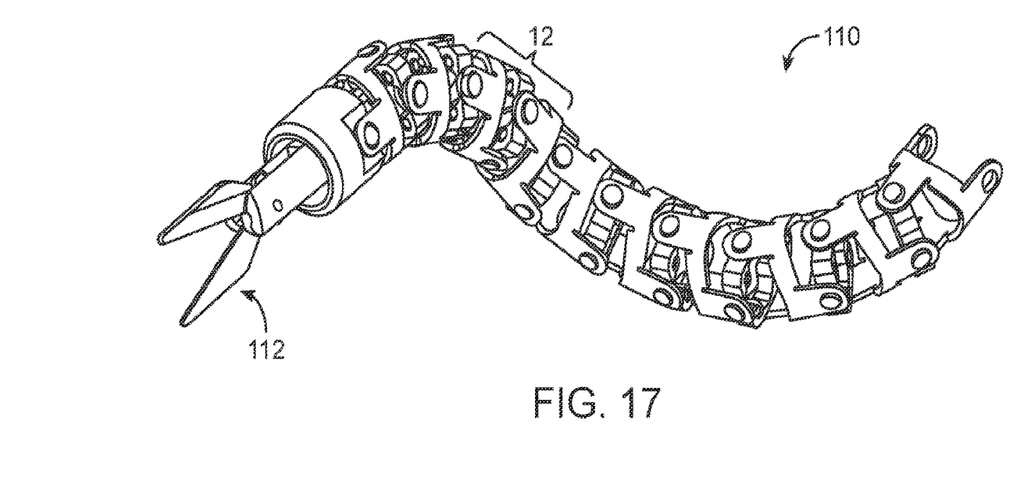
FIG. 17 is a perspective view of a portion of yet another embodiment of a robotic surgery tool, with a shears end effector.
Figure 18:
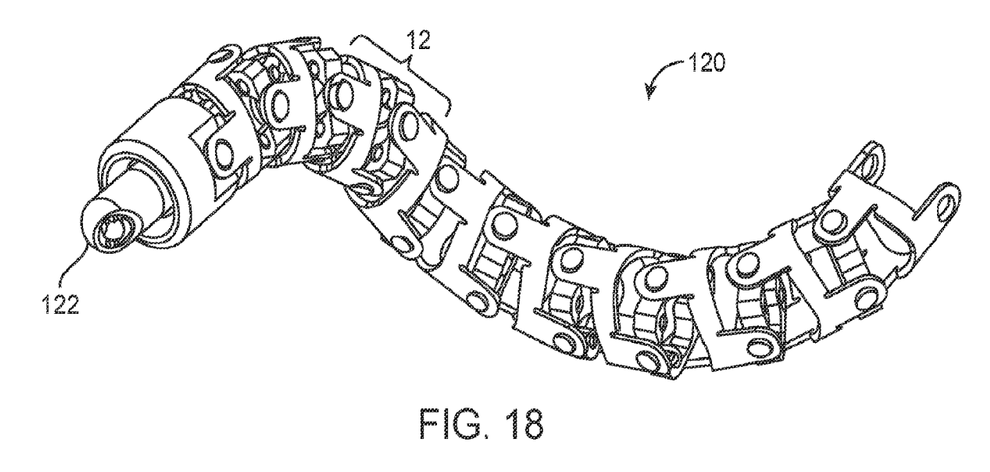
FIG. 18 is a perspective view of a portion of yet another embodiment of a robotic surgery tool, with a tissue debrider end effector.
Figure 19:
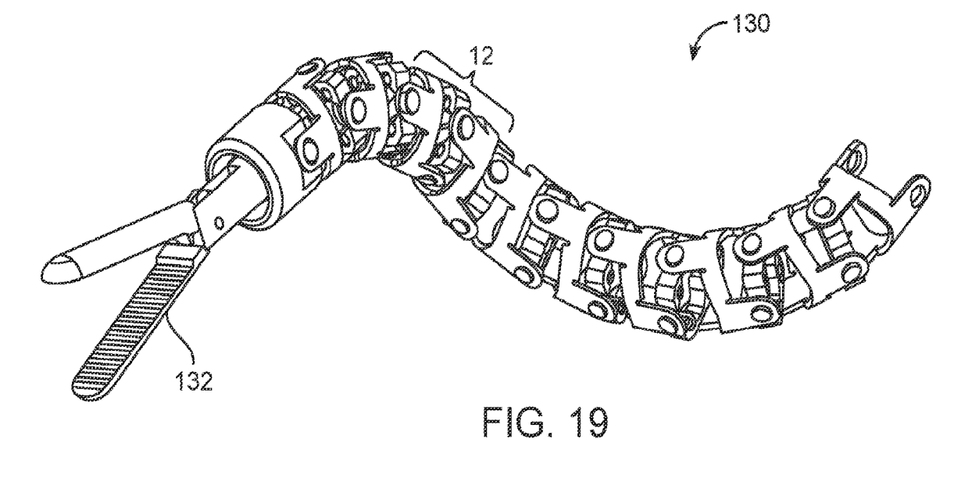
FIG. 19 is a perspective view of a portion of yet another embodiment of a robotic surgery tool, with a tissue sealing clamp/jaws end effector.

FIG. 16 is a perspective view of a distal portion of yet another embodiment of a robotic surgery tool 100, with the same configuration of joints 12 but with a biopsy brush end effector 102. FIG. 17 is a perspective view of a distal portion of yet another embodiment of a robotic surgery tool 110, with the same configuration of joints 12 but with a shears end effector 112. The shears 112 may be with or without radiofrequency (RF) tissue sealing. FIG. 18 is a perspective view of a distal portion of yet another embodiment of a robotic surgery tool 120, with the same configuration of joints 12 but with a tissue debrider end effector 122. FIG. 19 is a perspective view of a distal portion of yet another embodiment of a robotic surgery tool 130, with the same configuration of joints 12 but with a tissue sealing clamp/jaws end effector 132. As should be apparent from the embodiments of FIGS. 13-19, any suitable robotic surgery tool may include one or more link-yoke-link joints 12, as described herein. The particular end effector of any embodiment is not limited.

Figure 20:
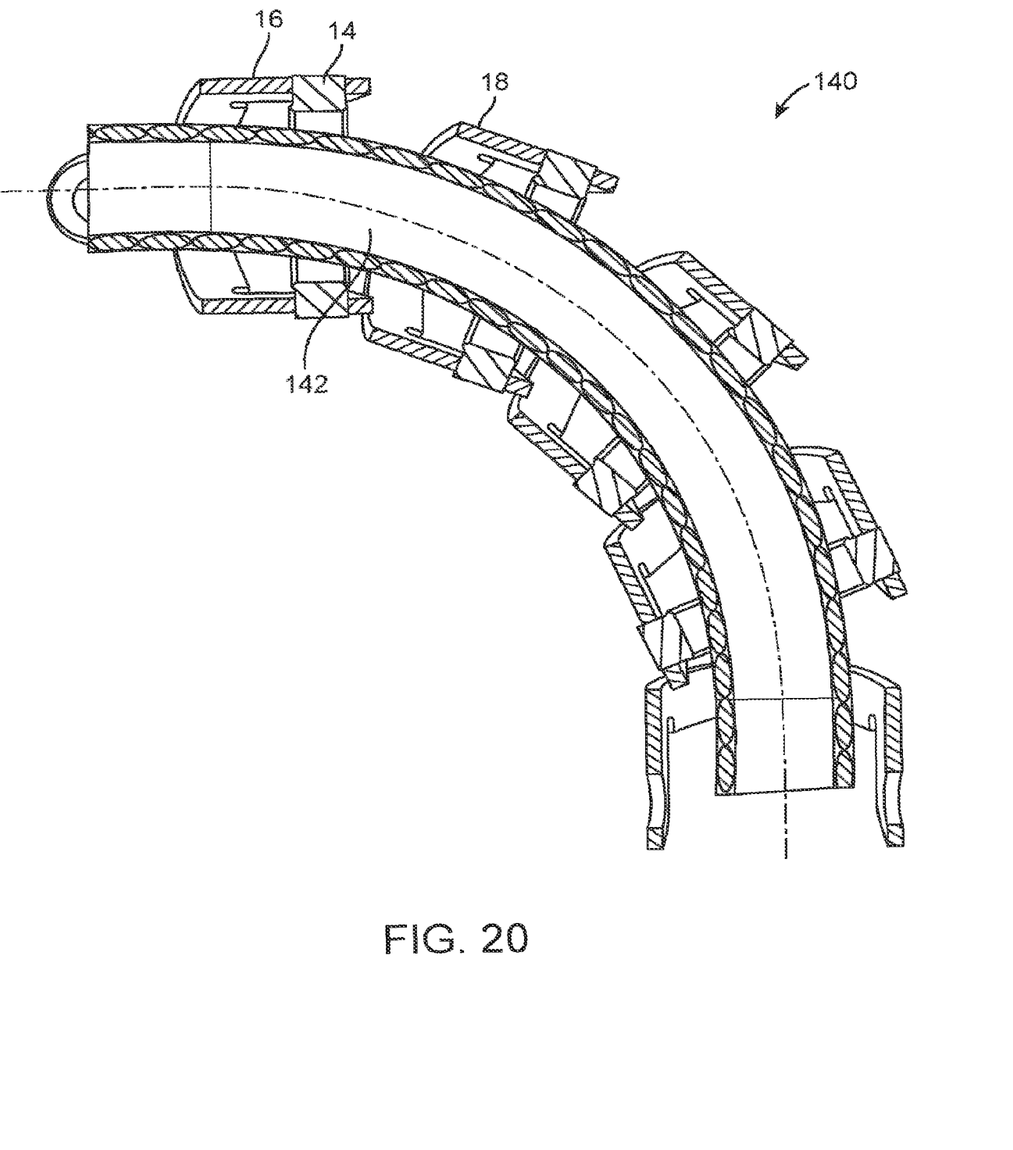
FIG. 20 is a side, cross-sectional view of a portion of yet another robotic surgery tool, including a drive shaft.

FIG. 20 is a side, cross-sectional view of a portion of yet another robotic surgery tool 140. Again, this tool 140 includes a number of joints, and it additionally includes a drive shaft 142 that extends through the lumen formed by the joints 12. The yokes allow for the smooth operation of a flexible drive shaft through the yokes because the link-yoke-link system follows the neutral axis for the radius of curvature. One advantage of the link-yoke-link joint 12 (or a multiple joint 12 device or system) is its precise radius of curvature, where the system neutral axis intersects the centerline of each link 16, 18. The through-hole in the yoke 14 directs the alignment of the rotary drive shaft 142 to intersect with a continuous radius of curvature through the neutral axis of the tool 140. This enhances operating conditions of a powered rotary robotic surgery tool 140, especially where high rotational speeds are necessary.

Because the central opening 24 of the joint is so large, any of a number of tools or tool components may pass through a given embodiment of the device 10. For example, any of the following instruments may pass through the device 10 to a distal end effector at the device's distal end: cameras and lighting; needle biopsy devices; brush biopsy devices; forceps biopsy devices; debrider biopsy devices; RF coagulation/cutting devices (monopolar, bipolar); probes; sealing devices; and the like. Similarly, the joints 12 and devices 10 described herein may be used or adapted for use in any suitable medical or surgical procedure, including but not limited to: debrider tumor resection, shears tumor resection, delivery of biologics and medications, neural tumor resection, polyp resection or biopsy, breast biopsy, lung biopsy, minimal portal access heart bypass, endoscopic submucosal dissection, transurethral procedures (TURP, bladder tumors) prostatectomy, hysterectomy, stem cell delivery, delivery of arthroscopic tools, knees and hips, and transnasal procedures (frontal sinus tissue removal, functional endoscopic sinus surgery, etc.). These are only examples, however, and any other end effectors and procedures may be used in various alternative embodiments.

The foregoing is believed to be a complete and accurate description of various embodiments of a universal joint for robotic surgery devices, various device incorporating such a joint, and methods of making and using such devices. The description above, however, is not intended to limit the scope of the claims that follow.

The invention claimed is:

1. A method for manipulating a robotic surgery tool, the method comprising:
    obtaining a robotic surgery tool with a proximal end and a distal end, said robotic surgery tool further comprising a plurality of joint devices, pull wires, and an end effector device;
    each said joint device comprising a link-yoke-link joint comprising a separate yoke pivotably coupled to two separate links on either side of said yoke, each link configured to pivot about said yoke at a right angle to the other link;
    each said yoke further comprising a plurality of pull wire holes;
    each of said plurality of pull wires configured to slidably pass through different pull wire holes in said yokes, and through a plurality of said joint devices, until said pull wires reach and attach to said end effector device;
    applying tension to a first pull wire to cause a first link of a joint device of the tool to pivot in a first plane relative to a yoke attached to the first link; and
    applying tension to a second pull wire to cause a second link attached to the yoke to pivot in a second plane orthogonal to the first plane; and
        using said first and second pull wires to direct said end effector to a desired target.

2. The method of claim 1, further comprising performing a function with said end effector of the robotic surgery tool.

3. The method of claim 2, wherein said yokes further comprise a central opening different from said plurality of pull wire holes; and said end effector extends from a said distal end of the robotic surgery tool toward said proximal end through said central opening in at least some of said yokes.

4. The method of claim 2, wherein the end effector is selected from the group consisting of a camera, an injection needle, a needle biopsy device, a brush biopsy device, forceps, a tissue debrider, scissors, an electrocautery device, and a radiofrequency device.

5. The method of claim 2, wherein the first and second pull wires extend from the end effector to a pull wire manipulator at or near said proximal end of said robotic surgery tool, and wherein applying tension to the first and second pull wires applies force to the end effector, which is transmitted to the joint device.

6. The method of claim 2, wherein applying the tension to at least one of the first pull wire and the second pull wire causes at least a third link to pivot relative to at least one additional yoke.

7. The method of claim 2, wherein manipulating the robotic surgery tool comprises performing part of a procedure selected from the group consisting of debrider tumor resection, shears tumor resection, delivery of biologics and medications, neural tumor resection, polyp resection or biopsy, breast biopsy, lung biopsy, minimal portal access heart bypass, endoscopic submucosal dissection, transurethral procedures, prostatectomy, hysterectomy, stem cell delivery, delivery of arthroscopic tools, and transnasal procedures.

8. The method of claim 1, wherein said joint comprises a square-shaped outer surface with four cylindrical pivot bosses extending laterally from four sides of said outer surface.

9. The method of claim 1, wherein said yokes further comprise a large central opening separated and distinct from said pull wire holes.

* * * * *